United States Patent [19]

Brooks et al.

[11] Patent Number: 5,790,249
[45] Date of Patent: Aug. 4, 1998

[54] FLOW CONTAMINATION TESTER

[75] Inventors: Richard V. Brooks; James E. Briddell; Robert L. Fuller; Kenneth E. Newman, all of Kingsport, Tenn.

[73] Assignee: Eastman Chemical Company, Kingsport, Tenn.

[21] Appl. No.: 774,289

[22] Filed: Dec. 23, 1996

[51] Int. Cl.[6] ................................................. G01N 21/53
[52] U.S. Cl. .............................. 356/335; 356/336; 356/338
[58] Field of Search .............................. 356/237, 335–343, 356/246, 129; 73/597, 54.41, 599, 644

[56] References Cited

U.S. PATENT DOCUMENTS

| | | | |
|---|---|---|---|
| 4,177,482 | 12/1979 | Henry | 358/93 |
| 4,509,360 | 4/1985 | Erwin et al. | 73/599 |
| 4,529,306 | 7/1985 | Kilham et al. | 356/338 |
| 4,910,403 | 3/1990 | Kilham et al. | 250/343 |
| 5,231,463 | 7/1993 | Shambaugh | 356/336 |
| 5,433,112 | 7/1995 | Piche et al. | 73/597 |
| 5,442,437 | 8/1995 | Davidson | 356/246 |

*Primary Examiner*—Hoa Q. Pham
*Attorney, Agent, or Firm*—Fish & Richardson P.C.

[57] ABSTRACT

Apparatus for measuring contamination in a hot melt flow. The apparatus includes a flow cell tube adapted to pass the melt flow. Apparatus is provided for directing laser energy through the tube and the melt flow passing through the flow cell tube to a laser energy detector producing an electrical signal representative of the size of a contaminant in the flow melt. A heater is provided for heating the melt flow as such melt flow passes through the flow cell tube. The apparatus is adapted to measure contamination in a hot melt where the temperature of the melt must be maintained as the melt passes through the flow tube. The flow tube, laser, detector and heater are disposed within a housing. The housing has a cooling chamber. The detector is disposed in the cooling chamber to thermally isolate the detector from the heating of the flow.

16 Claims, 2 Drawing Sheets

Figure 1:
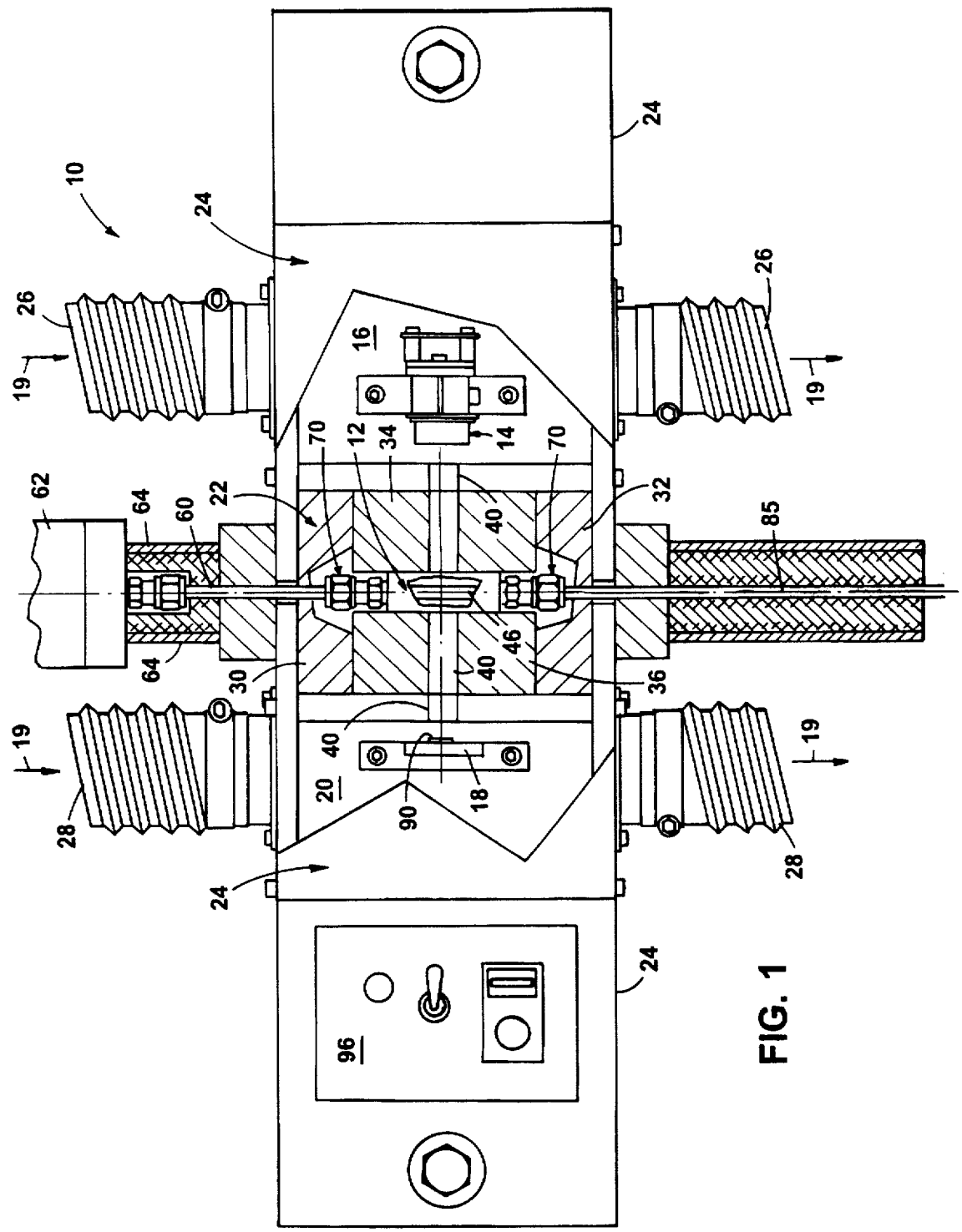
Figure 2:
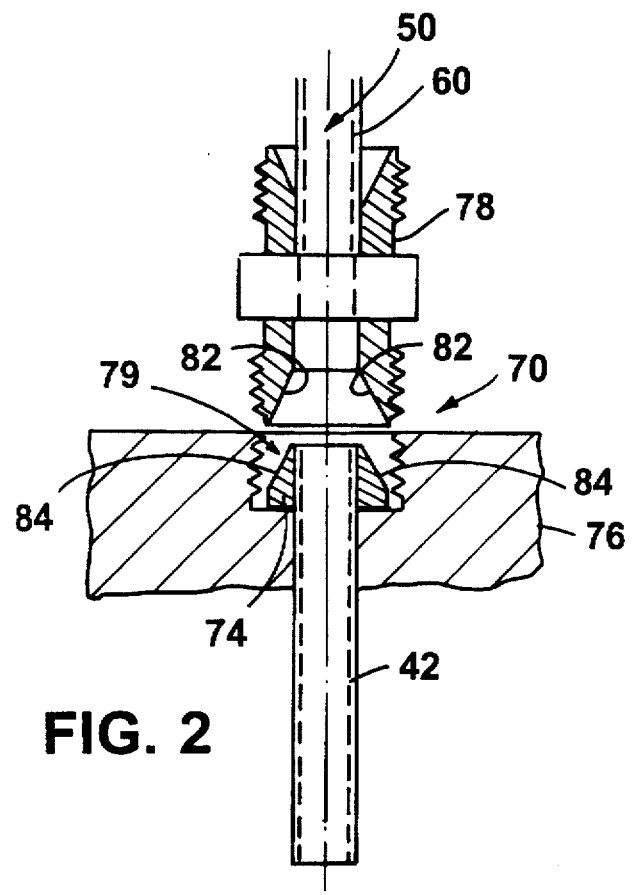
Figure 3:
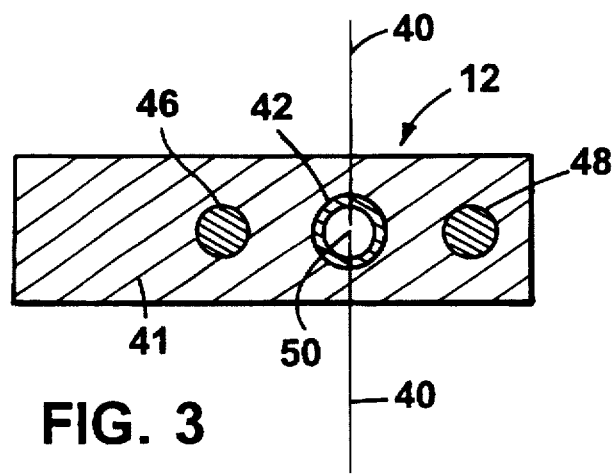

FLOW CONTAMINATION TESTER
>
> ## BACKGROUND OF THE INVENTION
>
> This invention relates generally to flow contamination testers and more particularly to flow contamination testers adapted to count and size contaminants in a hot melt flow.
>
> As is known in the art, it is sometimes desirable to monitor the amount and size of contaminants in a stream of material. An on-line device for analyzing contaminant particle size and count would enable an early assessment of the quality of the material.
>
> One known contamination tester analyzes contamination in a acetate doped stream. With such tester, a stream of acetate doped material is pumped at low rates through a laser energy transparent tube. A low power laser is positioned to shine laser energy though the tube and the stream passing through the tube onto a laser detector. The detector has an opaque mask at its central region and along the central axis of the laser beam to block the detected from any non-deflected laser energy. When a particle or material (i.e., a contaminant) of different light refraction from the main material, here acetate doped, the laser beam is diverted from the central axis and is therefore not masked by the opaque mask. Thus, the contaminate deflects the laser beam onto an un-blocked region of the detector. The detector produces an output signal proportional to the amount of laser energy intercepted by the detector. Because the amount of laser energy intercepted by the detector increases with the amount of deviation of the laser beam from the optic axis, and because the amount of deflection from the optic axis is proportional to the size of the contaminant, it follows that the output signal produced by the detector is proportional to the size of the contaminant. The signal produced by the detector is amplified, digitized and passed to a computer. The computer analyzes the signal and computes contaminant count and size. Calibration of particle size is accomplished using beads (i.e., contaminants) of known size in the stream.
>
> Another system used to measure contaminants is described in U.S. Pat. No. 4,177,482 issued Dec. 4, 1979, inventor James W. Henry.
>
> ## SUMMARY OF THE INVENTION
>
> In accordance with one feature of the invention apparatus is provided for measuring contamination in a hot melt flow. The apparatus includes a flow cell tube adapted to pass the melt flow. Apparatus is provided for directing laser energy through the tube and the melt flow passing through the flow cell tube to a laser energy detector producing an electrical signal representative of the size of a contaminant in the flow melt. A heater is provided for heating the melt flow as such melt flow passes through the flow cell tube.
>
> With such an arrangement, apparatus is provided for measuring contamination in a hot melt where the temperature of the melt must be maintained as the melt passes through the flow tube.
>
> In accordance with another feature of the invention, the flow tube, laser, detector and heater are disposed within a housing. The housing has a cooling chamber. The detector is disposed in the cooling chamber. With such an arrangement, the detector is thermally isolated from the heating of the flow as such flow passes though the flow tube.
>
> In accordance with another feature of the invention, the housing has a second cooling chamber for the laser. With such an arrangement, the laser is thermally isolated from the heating of the flow as such flow passes though the flow tube.
>
> In a preferred embodiment, the chambers pass a fluid at a temperature to cool the laser and the detector to temperatures below 100° F.
>
> In accordance with another feature of the invention, the melt flow is introduced into the flow cell tube through an input tube. A fitting is provided having one end attached to one end of the flow cell tube and a second end adapted for coupling to the input tube.
>
> In accordance with still another feature of the invention, the apparatus include a ferrule seal attached to said end of the flow cell tube and disposed within a threaded pocket of a housing. The fitting has an inner surface configured to engage the ferrule seal when threaded into the threaded pocket providing a seal for the melt flow as such melt flow passes into the flow cell tube from the input tube.
>
> In accordance with still another feature of the invention, the heater heats the melt flow to a temperature in the order of 350° C. With such an arrangement, the melt may be a melt flow of a polymer, such as polyethylene terephthalate (PET).
>
> ## BRIEF DESCRIPTION OF THE DRAWING
>
> Other features of the invention, as well as the invention itself, will become more readily apparent when read together with the accompanying drawings, in which:
>
> FIG. 1 is a diagrammatical sketch, partially broken away of a flow contamination tester according to the invention;
>
> FIG. 2 is a cross sectional drawing of one of a pair of fittings used in the tester of FIG. 1; and
>
> FIG. 3 is a top view of a fixture used to hold a flow tube and a pair of cartridge heaters used in the tester of FIG. 1.
>
> ## DESCRIPTION OF THE PREFERRED EMBODIMENTS
>
> Referring now to FIG. 1, a melt flow polymer contamination tester 10 is shown. The tester 10 includes a flow cell 12 adapted to pass the melt flow. The tester 10 includes a laser 14, disposed in a laser cooling chamber 16, and a laser energy detector 18, disposed in a detector cooling chamber 20. The flow cell 12 is disposed in a central chamber 22 disposed between the laser and detector chambers 16, 20. The flow cell 12, laser 14 and detector 18 are disposed in a common housing 24. Here, the laser and detector chambers 16, 20 pass a fluid (represented by arrows 19) at a temperature to cool the laser and the detector to temperatures below 100° F. introduced through conduits 26, 28.
>
> The central chamber 22 has top and bottom insulating blocks 30, 32, and top and bottom middle insulating blocks 34, 36, as shown. The laser 14 produces a beam of laser energy which passes between the upper and lower heat insulating blocks 34, 36 along a horizontally disposed optic axis 40 aligned with the center of the detector 18, as indicated. Disposed through a vertically disposed central region of the upper and lower middle heat insulating blocks 34, 36 is a flow cell 12 shown in FIG. 3. More particularly, the flow cell 12 is a stainless steel block 41 having a centrally disposed hole passing through it for the flow tube 42. A pair of holes is provided on either side of the central, flow tube hole, for a pair of electrical cartridge heaters 46, 48, here No. E2A56 Watlow Firerod cartridge heater 0.25 inches in diameter and 2 inches long, operated by a 120 volt supply, not shown in controller 96, at 150 watts. The heaters 46, 48 are electrically connected by wires, not shown, which pass through holes, not shown, in insulating block 34 to controller 96. The optic axis 40 is shown in FIG. 3. It is noted from FIGS. 1 and 3 that the cartridge heaters 46, 48 are not disposed in the path of the laser energy and that the laser energy is directed through the flow cell tube 42 and melt flow 50 passing through the flow cell tube 42 to the laser energy detector 18. In response to laser energy detected by the detector 18, the detector 18 produces an electrical signal representative of the size of a contaminant in the flow melt 50 in a manner to be described. It is noted that the heaters 46, 48 are provided for heating the melt flow 50 as such melt flow 50 passes through the flow cell tube 42. Here, the heaters 46, 48 heat the melt flow 50 to a temperature in the order of 350° C. The apparatus is adapted to measure contamination in a hot melt where the temperature of the melt must be maintained as the melt passes through the flow tube 42.

The melt flow 50 (FIG. 3) is introduced into the flow cell tube 42 through an input tube 60, here stainless steel. The melt flow 50 stream is provided to the tester from melt flow processing equipment such as a melt extruder or melt pump 62. The melt flow 50 can be processed through the tester 10 at temperatures up to about 350° C. and pressure to 2000 psi. The stainless steel input tube 60 is disposed within a strip heater 64 to maintain the melt flow 50 at a proper temperature. The melt flow 50 is fed from the stainless steel input tube 60 to the flow tube 42 via a fitting 70, shown in FIG. 2. The flow tube 42 is substantially transparent to the laser energy. More particularly, the flow tube 42 is here clear 99+% aluminum oxide having an outside diameter of 0.250±055 inches and a wall thickness of 0.050±008 inches wall thickness. The fitting 70, shown more clearly in FIG. 2, is provided for each end of the flow tube 42. Each fitting 70 has one end attached to one end of the flow cell tube 42 and a second end adapted for coupling to the input tube 60 (or output stainless steel tube 85 (FIG. 1)). The joint between the stainless steel tube 60 (or tube 85) and aluminum oxide flow tube 42 must be capable of experiencing many heat cycles with thermal expansion and contraction without leaking. The fitting 70 (FIG. 2) includes a graphite ferrule 74 (here Supeltex M4, no. 2-2492, manufactured by Supelco Inc. Belefonte, Pa.) mounted on each end of the aluminum oxide flow tube 42. A thread for a Swagelok ¼" union 78 manufactured by Crawford Fitting Co. of Solon, Ohio, is machined into the housing for the flow tube 42. The union 78 is then threaded into a hole 79 and seats against the graphite ferrule. The seal thus formed between the tubes 42, 60 has performed through many heat cycles with no leakage. It is noted that each fitting 70 has an inner surface of the union 78 tapered to engage, and mate with, an outer tapered surface 84 of the ferrule seal 74 when threaded into the threaded pocket thereby providing a seal for the melt flow as such melt flow 50 passes into the flow cell tube 42 from the input tube 60. After flowing through, the transparent flow tube 42, the melt then flows through another heated stainless steel tube 85 (FIG. 1) to either waste or another melt stream.

A collimated laser beam is provided by the laser 14 along axis 40 perpendicular to the longitudinal axis of the clear flow tube 42 through which the melt 50 flows (i.e., the optic axis 40 is perpendicular to the direction of the flow of melt 50. Here the laser 14 a Gallium-aluminum-arsenide light-emitting diode provided by D. O. Industries, Rochester, N.Y. It is rated at 25 milliwatts output. The laser 14 is mounted so that the delivery end is about 2 to 5 inches from the flow tube 42. The photodetector 18, as noted above, is mounted on the opposite side of the tube 42 from the laser 14 and about 2 to 5 inches from the flow tube 42. A mask 90, opaque to the laser energy, approximately 0.06 inches wide is disposed perpendicular to the optic axis and is used to mask the main beam of the laser 14. When defective flow particles in the melt 50 come through the flow tube 42, the laser beam is deflected off the optic axis 40 and by-passes the mask 90 to impinge onto the photodetector 18. The signal from the photodetector 18 is transmitted to an amplifier, not shown, which amplifies the analog signal and sends it to a processor 96 housed within the housing 24. The strength, or level of the analog signal is proportional to the size of the defective particle, i.e., contaminant, in the flow melt 50. The processor 96 converts the signal from an analog signal to a corresponding digital signal. The processor in executing a computer software program collects the digital signals and convert them into a report of contaminant counts and size distribution.

As noted above, the apparatus tester 10 includes laser 14 and detector 18 cooling side chambers 16, 20 designed to cool the laser 12 and detector 18 while also providing a center chamber 22 through which the melt flows heated to high temperatures for polymer melts. The side chambers 16, 20 in which the laser and photodetector reside are cooled to a temperature below 100° F. to protect the electronic components. The cooling of these chambers 16, 20, 22 is accomplished using air blowers, one for each chambers 16, 20, 22, via conduits 28, as described above. The center chamber 22 is heated with electrical cartridge heaters 46, 48. Other types of cooling could be used on the side chambers, such as water coils. A special type of insulation blocks 30, 32, 34, 36 was used to insulate the center chamber from the chambers 16, 20 and housing 24. The heat insulating blocks are a ceramic fiber insulation block fabrication from 43% alumina and 57% silica. The R-value of this insulation is 2.95/in @70° F. and temperature range is −280° to 2300° F.

The tester 10 is useful for analyzing any liquid or melt flow stream that does not have an excessive amount of fillers to block light passing through the flow media. The analysis would consist of counting the sizing particles or materials foreign to the main flow media. Examples of applications are analysis of particles or gels in a polymer melt flow stream for quality control, analysis of particles in water for purification tests.

Another application for the tester 10 would be to characterize residence time distributions for an extruder or other polymer processing machines. A tracer material of known size is added into the feed of the extruder and particle counts are made versus time using the melt flow polymer contamination tester.

EXAMPLES

Example 1

Polypropylene 424S material previously manufactured by Eastman Chemical of Kingsport, Tenn. was extruded and pumped through the flow cell of the melt flow polymer contamination tester (PCT) 10 at 5–6 g/min. Melt temperature was 230° C. and set point temperatures on the melt PCT 10 were 230° C. Six one-minute trials were run in which defective particles were counted and sized into ranges starting with 10 micron on the small end. This initial test of the tester 10 proved it is capable of counting the sizing defective particles in a hot melt flow stream.

Example 2

A test similar to Example 1 was run except the feed was spiked with glass beads (126±6.3 micron diameter) for test of the calibration of the tester 10. After about 4 minutes the counts in the range of 123–130 micron increased from 0 to 0.038,0.038,0.182,0.112 parts per million (ppm) for minutes 5–8 of the trial; counts in the range of >130 increased from 0 at 4 min. to 0.089,0.135,0.228,0.095 for minutes 5–8 of the trial. It is concluded that the approximate sizing of the particles by the tester 10 is in the proper range.

Example 3

A test was run using a good sample of Thermx copolyester material manufactured by Eastman Chemical Kingsport, Tenn. and Thermx material containing black specs. The test was run at 20–23 g/min at melt temperature of about 270° C. A pressure drop of about 500–600 psi was measured across the melt PCT at extruder speed of 30 rpm. A significantly higher count was recorded for particle counts higher than 61 micron, the probable size of the black specks. Thus the tester is capable of distinguishing good Thermx material from Thermx material with unacceptable level of black specs. The test also confirmed previous tests that the apparatus 10 is capable of analyzing a hot polymer melt at elevated temperatures.

Other embodiments are within the spirit and scope of the appended claims.

What is claimed is:

1. Apparatus for measuring contamination in a melt flow, comprising:

a flow cell tube, having walls of laser energy transparent material, adapted to pass the melt flow;

apparatus for directing laser energy through the laser transparent material of the walls of the flow cell tube and the melt flow passing through the flow cell tube to a laser energy detector producing an electrical signal representative of the size of a contaminant in the flow melt; and a heater for heating the melt flow as such melt flow passes through the flow cell tube.

2. The apparatus recited in claim 1 wherein the melt flow is introduced into the flow cell tube through an input tube, and including a fitting having one end attached to one end of the flow cell tube and a second end adapted for coupling to the input tube.

3. The apparatus recited in claim 2 including:

a ferrule seal attached to said end of the flow cell tube and disposed within a threaded pocket of a housing; and wherein the fitting has an inner surface configured to engage the ferrule seal when threaded into the threaded pocket providing a seal for the melt flow as such melt flow passes into the flow cell tube from the input tube.

4. The apparatus recited in claim 3 wherein the heater heats the melt flow to a temperature in the order of 350° C.

5. The apparatus recited in claim 4 wherein the ferrule seal is graphite.

6. The apparatus recited in claim 1 wherein the housing has a cooling chamber and wherein the detector is disposed in the cooling chamber.

7. The apparatus recited in claim 6 wherein the housing has a second cooling chamber and wherein the second cooling chamber has the laser disposed therein.

8. The apparatus recited in claim 7 wherein the chambers pass a fluid at a temperature to cool the laser and the detector to temperatures below 100° F.

9. The apparatus recited in claim 8 wherein the housing has a cooling chamber and wherein the detector is disposed in the cooling chamber.

10. The apparatus recited in claim 9 wherein the housing has a second cooling chamber and wherein the second cooling chamber has the laser disposed therein.

11. The apparatus recited in claim 10 wherein the chambers pass a fluid at a temperature to cool the laser and the detector to temperatures below 100° F.

12. Apparatus for measuring contamination in a melt flow, comprising:

a flow cell tube, comprising:
a thermally conductive block having a hole passing therethrough;
a flow tube disposed in the hole, such flow tube having walls of laser energy transparent material, such tube being adapted to pass the melt flow;
a heater cartridge, mounted in, and thermally coupled to, the block for heating the melt flow as such melt flow passes through the flow cell tube;

apparatus for directing laser energy along an optic path through the melt flow passing through the flow tube to a laser energy detector producing an electrical signal representative of the size of a contaminant in the flow melt, such laser energy passing through the laser energy transparent material of the tube; and wherein the heater cartridge is displaced from the optic axis and heats the melt as the flow passes through the hole in the block.

13. The apparatus recited in claim 12 wherein the melt flow is introduced into the flow cell tube through an input tube, and including a fitting having one end attached to one end of the flow cell tube and a second end adapted for coupling to the input tube.

14. The apparatus recited in claim 13 including:

a ferrule seal attached to said end of the flow cell tube and disposed within a threaded pocket of a housing; and wherein the fitting has an inner surface configured to engage the ferrule seal when threaded into the threaded pocket providing a seal for the melt flow as such melt flow passes into the flow cell tube from the input tube.

15. The apparatus recited in claim 14 wherein the heater heats the melt flow to a temperature in the order of 350° C.

16. The apparatus recited in claim 15 wherein the ferrule seal is graphite.

* * * * *